United States Patent
Ariga et al.

(10) Patent No.: US 9,390,324 B1
(45) Date of Patent: Jul. 12, 2016

(54) IMAGE PROCESSING DEVICE AND METHOD OF IMAGE PROCESSING

(71) Applicant: MITUTOYO CORPORATION, Kanagawa (JP)

(72) Inventors: Kozo Ariga, Kawasaki (JP); Masaru Kawazoe, Kawasaki (JP)

(73) Assignee: MITUTOYO CORPORATION, Kanagawa (JP)

( * ) Notice: Subject to any disclaimer, the term of this patent is extended or adjusted under 35 U.S.C. 154(b) by 0 days.

(21) Appl. No.: 15/070,148

(22) Filed: Mar. 15, 2016

Related U.S. Application Data (63) Continuation of application No. 13/545,269, filed on Jul. 10, 2012, now abandoned.

(30) Foreign Application Priority Data

Feb. 21, 2012 (JP) ................................. 2012-034779

(51) Int. Cl.
*H04N 7/18* (2006.01)
*G06K 9/00* (2006.01)

(52) U.S. Cl.
CPC ........ *G06K 9/00536* (2013.01); *G06K 9/00503* (2013.01)

(58) Field of Classification Search
None
See application file for complete search history.

(56) References Cited

U.S. PATENT DOCUMENTS

| | | | | |
|---|---|---|---|---|
| 6,798,923 B1* | 9/2004 | Hsieh | ...................... | G06T 3/403 345/629 |
| 2005/0265593 A1* | 12/2005 | Hauck | ...................... | G01N 3/08 382/141 |
| 2006/0256397 A1* | 11/2006 | Cui | ........................ | G06T 7/0028 358/450 |
| 2007/0084927 A1* | 4/2007 | Itou | ..................... | G06K 7/10722 235/454 |
| 2010/0329586 A1* | 12/2010 | Stellari | ................. | G06T 7/0026 382/284 |

FOREIGN PATENT DOCUMENTS

| | | | | |
|---|---|---|---|---|
| CN | 1949833 A | 4/2007 | | |
| CN | 101937055 A | 1/2011 | | |
| JP | 63-54680 | 3/1988 | | |
| JP | 4-157577 | 5/1992 | | |
| JP | 8-313217 | 11/1996 | | |
| JP | 9-281405 | 10/1997 | | |
| JP | 11-289199 A | 10/1999 | | |
| JP | 11-331556 A | 11/1999 | | |
| JP | 11331556 A | * 11/1999 | ............ | G06T 3/4038 |
| JP | 2005-345117 | 12/2005 | | |
| JP | 2008-510201 | 4/2008 | | |
| JP | 2010-190817 | 9/2010 | | |

* cited by examiner

*Primary Examiner* — Sath V Perungavoor
*Assistant Examiner* — Dakshesh Parikh
(74) *Attorney, Agent, or Firm* — Greenblum & Bernstein, P.L.C.

(57) ABSTRACT

A control unit shifts an imaging unit relatively with respect to a stage to take an image of a measuring object at a plurality of places by the imaging unit and thereby obtain a plurality of images, and generates a composite image of the measuring object having a range which is wider than an imaging range of the imaging unit by combining the plurality of images. The control unit shifts the imaging unit relatively with respect to the stage such that parts of images adjacent to one another obtained by the imaging unit overlap, and performs an image matching processing that performs image matching of an overlapped portion of the adjacent images. The control unit generates the composite image of the measuring object by joining the adjacent images at a position where the image matching is performed in the image matching processing.

18 Claims, 9 Drawing Sheets

Binarize Overlapping Region Images RIM(1), RIM(2) to Generate Binarized Images BIM(1), BIM(2)

FIG. 8

Extract Outline From Overlapping Region Images RIM(1), RIM(2) to Generate Edge Images EIM(1), EIM(2)

IMAGE PROCESSING DEVICE AND METHOD OF IMAGE PROCESSING

CROSS-REFERENCE TO RELATED APPLICATIONS

This present application is a continuation application of pending U.S. patent application Ser. No. 13/545,269, filed Jul. 10, 2012, which is based upon and claims the benefit of priority from the prior Japanese Patent Application No. 2012-34779, filed on Feb. 21, 2012, the entire contents of which are incorporated herein by reference.

BACKGROUND OF THE INVENTION

1. Field of the Invention

This invention relates to an image processing device employed in the likes of a hardness testing device and a method of image processing.

2. Description of the Related Art

A hardness testing device that measures hardness of a measuring object based on a shape of an indentation formed in a surface of the measuring object, is known (refer to JP 2010-190817 A and JP 2005-345117 A). In this hardness testing device, the measuring object is disposed on a stage and a measured value of hardness of the measuring object is obtained using an image of the measuring object capable of being taken by an imaging device. When the image shows only a region of part of the measuring object, an entire image showing the measuring object is necessary. Thus, conventionally, a method that shifts the stage relatively in a certain direction to take a plurality of images and joins these plurality of images to generate a composite image, is known (refer to JP H08-313217 A).

However, in the above-described method for generating a composite image, if directions of coordinate axes of the image and directions of coordinate axes of the stage are not in parallel, then in a portion where the image is joined, the composite image becomes discontinuous and errors are generated in coordinate values of the image in a coordinate system of the stage. This problem is solved if an attitude of the imaging device is physically adjusted such that directions of the coordinate axes of the image and the coordinate axes of the stage are matched. However, that adjustment is laborious and adjustment costs are also required.

The present invention was made in view of such a problem and has an object of providing an image processing device and a method of image processing capable of generating a composite image having no discontinuity at a composite portion, easily and at low cost.

SUMMARY OF THE INVENTION

An image processing device according to the present invention comprises: an imaging unit for taking an image of a measuring object; a stage configured to be mountable with the measuring object and to be shiftable relatively with respect to the imaging unit; and a control unit for shifting the imaging unit relatively with respect to the stage to take an image of the measuring object at a plurality of places by the imaging unit and thereby obtain a plurality of images, and for generating a composite image of the measuring object having a range which is wider than an imaging range of the imaging unit by combining the obtained plurality of images or images obtained by a certain processing from the obtained plurality of images, the control unit shifting the imaging unit relatively with respect to the stage such that parts of images adjacent to one another obtained by the imaging unit overlap, the control unit performing an image matching processing that performs image matching of an overlapped portion of the adjacent images, and the control unit generating the composite image of the measuring object by joining the adjacent images at a position where the image matching is performed in the image matching processing.

DETAILED DESCRIPTION OF THE EMBODIMENTS

Next, embodiments of the present invention are described in detail with reference to the drawings.

First Embodiment

Figure 1:
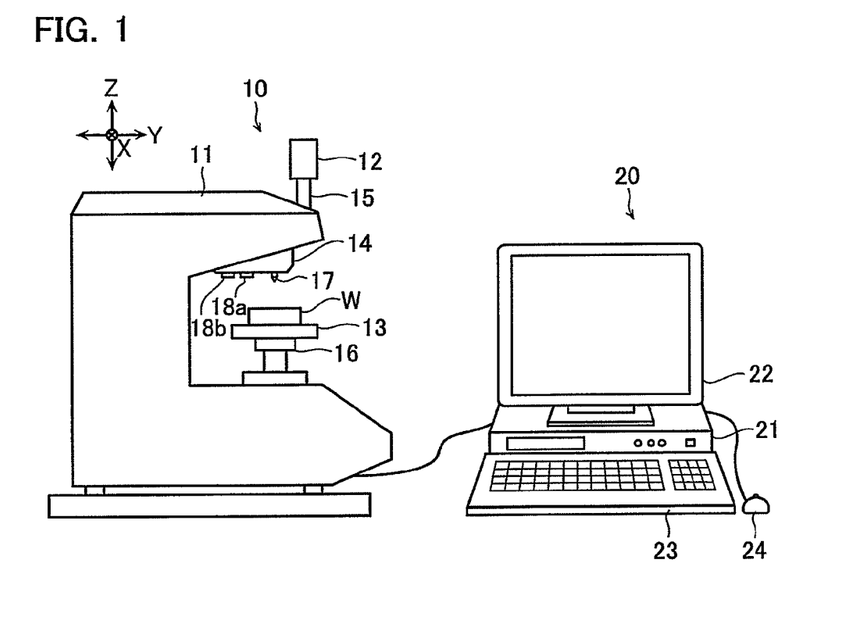
FIG. 1 is a schematic view showing a hardness testing device according to a first embodiment.

FIG. 1 is a schematic view showing a hardness testing device according to the present embodiment. As shown in FIG. 1, the hardness testing device includes a hardness testing machine 10 and a computer system 20 for controlling the hardness testing machine 10. Note that in the present embodiment, the hardness testing device functions also as an image processing device for generating a composite image.

The hardness testing machine 10 includes a support 11, an imaging unit 12, a stage 13 and a turret 14. The support 11 has a C shape when viewed from an X direction (perpendicular direction to paper plane in FIG. 1). The imaging unit 12 is provided on an upper portion of the support 11 and takes an image of a workpiece W (measuring object) via a camera mount 15. The imaging unit 12 is configured by, for example, a CCD camera or a CMOS camera.

The stage 13 is provided on a lower side of the support 11 via a shifting mechanism 16. The shifting mechanism 16 is configured such that the stage 13 is shiftable in an X axis direction, a Y axis direction, and a Z axis direction that are orthogonal to one another. That is, the shifting mechanism 16 is configured such that the imaging unit 12 is shiftable relatively with respect to the stage 13. The shifting mechanism 16 is controlled by the computer system 20 to drive the stage 13.

The turret 14 is provided on an upper portion of the support 11. The turret 14 is configured rotatable around a turret rotating shaft parallel to the Z axis, and includes on its lower side an indenter 17 and objective lenses 18a and 18b. The indenter 17 is for being pressed onto the workpiece W to make an indentation in a surface of the workpiece W. The objective lenses 18a and 18b are each for configuring an imaging optical system along with the imaging unit 12. Rotation of the turret 14 allows the indenter 17 and the objective lenses 18a and 18b to be switchably disposed to a usage position.

Figure 2:
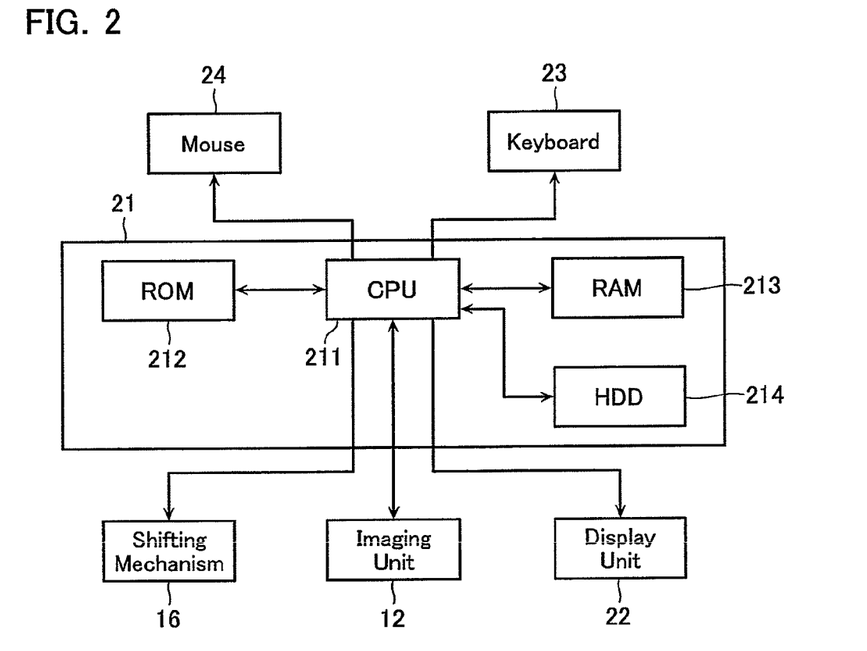
FIG. 2 is a block diagram showing a computer main body 21 according to the first embodiment.

The computer system 20 includes a computer main body 21, a display unit 22 which is a liquid crystal panel or the like, a keyboard 23 and a mouse 24. As shown in FIG. 2, the computer main body 21 includes, for example, a CPU 211, a ROM 212, a RAM 213 and a HDD 214. The CPU 211 executes processing according to a macro-program stored in the ROM 212 and a program stored in the RAM 213 from the HDD 214. The CPU 211 controls the imaging unit 12, the shifting mechanism 16 and the display unit 22 according to the programs. In addition, the CPU 211 receives input information from the keyboard 23 and the mouse 24.

Figure 3:
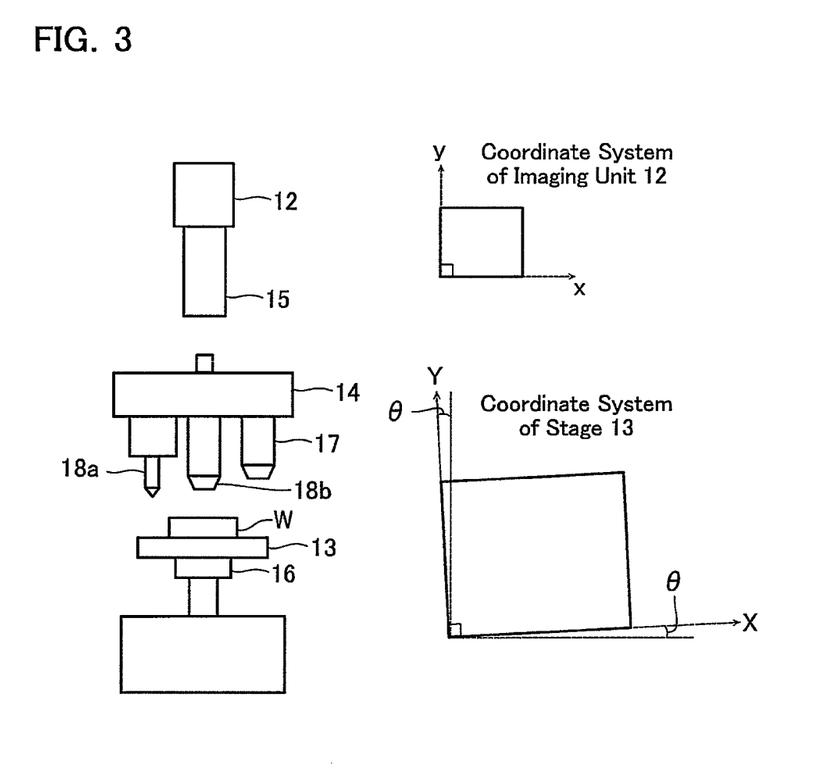
FIG. 3 is a schematic view showing misalignment of a coordinate system of an imaging unit 12 and a coordinate system of a stage 13.

Next, a coordinate system of the hardness testing device according to the present embodiment is described with reference to FIG. 3. As shown in FIG. 3, the present embodiment includes a coordinate system (x, y) of the imaging unit 12 and a coordinate system (X, Y) of the stage 13. Now, an axis x and an axis y are mutually orthogonal and are axes set in an image obtained by the imaging unit 12. An axis X and an axis Y are mutually orthogonal and are directions in which the stage 13 is shiftable. Note that the axis x and the axis y may also be axes set in an image obtained by the imaging unit 12 and that has undergone a certain processing.

As shown in FIG. 3, the coordinate system (X, Y) of the stage 13 has an angle θ with the coordinate system (x, y) of the imaging unit 12. Now, for example, an image is taken of the workpiece W while shifting the stage 13 by an amount of a certain distance in an X axis direction to obtain a plurality of images, and those plurality of images, while being displaced by an amount of a certain distance in an x axis direction, are joined to generate a composite image. However, in this method, due to misalignment by the angle θ, that composite image becomes a discontinuous image different to the actual workpiece W. As a result, there is a problem that, when an indentation position is disposed on this composite image and an indentation made in the workpiece W, it sometimes occurs that the position is misaligned, and hardness testing of a targeted place may not necessarily be performed.

Figure 4:
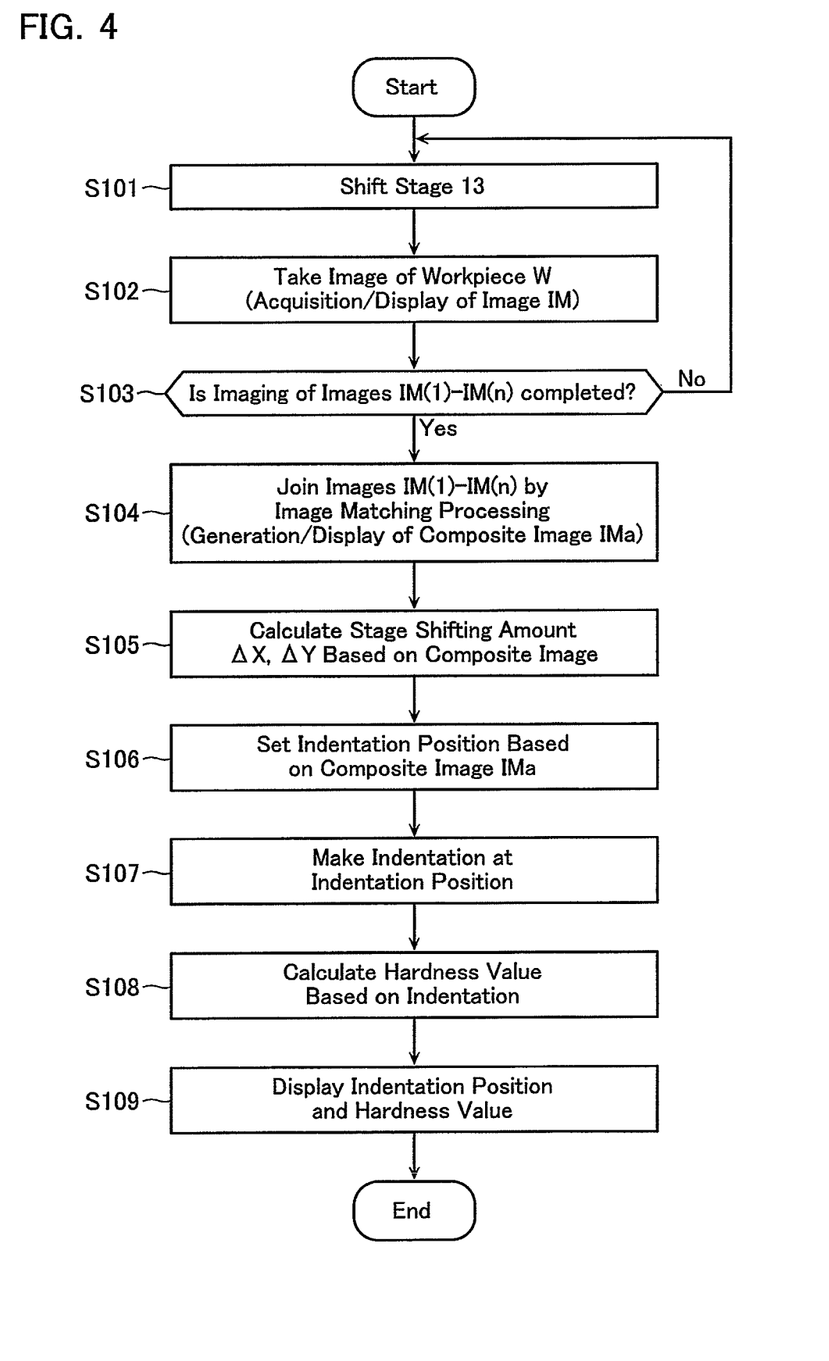
FIG. 4 is a flowchart showing operation of the hardness testing device according to the first embodiment.

Therefore, in the present embodiment, a composite image IMa is generated using a processing of the kind shown in FIG. 4. Note that control shown in FIG. 4 is executed by the CPU 211. As shown in FIG. 4, first, the stage 13 is shifted in a certain direction (S101). Next, an image is taken of the workpiece W by the imaging unit 12 to obtain an image IM (S102). In step S102, the image IM is displayed in the display unit 22. Then, it is judged whether a certain number of images IM(1)-IM(n) have been taken or not (S103). Now, if it is judged that the images IM(1)-IM(n) have not been taken (S103, No), then processing is executed again from step S101. On the other hand, if it is judged that the images IM(1)-IM(n) have been taken (S103, Yes), then the images IM(1)-IM(n) are joined by an image matching processing mentioned later to generate the composite image IMa (S104). Now, the composite image IMa is an image of the workpiece W having a range which is wider than a one-shot imaging range of the imaging unit 12. In step S104, the composite image IMa is displayed in the display unit 22. Note that the composite image IMa may be configured capable of being printed by a printer. Then, shifting amounts ΔX and ΔY of the stage 13 (stage shifting amounts) in the X axis and Y axis directions in which the stage 13 is shiftable are calculated based on the composite image IMa (S105). Note that, as mentioned later, shifting of the imaging unit 12 is controlled based on these stage shifting amounts.

Subsequent to step S105, an indentation position is set based on the composite image IMa (S106). For example, a shape of the workpiece W is recognized from the composite image IMa, and the indentation position is disposed automatically from the shape of that workpiece. Alternatively, by using the keyboard 23 and the mouse 24 to designate any position on the composite image IMa displayed in the display unit 22, the indentation position is disposed manually in that designated position.

Next, the indenter 17 is pressed onto the surface of the workpiece W to make an indentation in the disposed indentation position (S107). Then, an image is taken of this indentation, and a hardness value calculated based on a shape (size) of the indentation (S108). Then, this indentation position (coordinate value on the composite image) and the hardness value corresponding to that position are displayed in the display unit 22 (S109).

Figure 5:
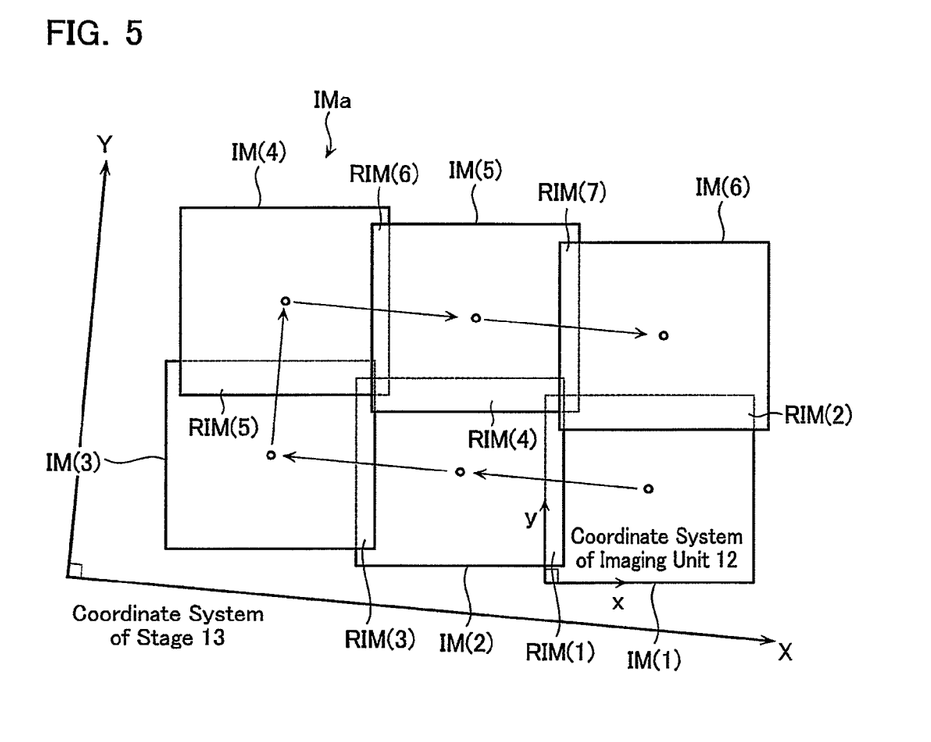
FIG. 5 is a schematic view showing shifting of the stage 13, imaging of a workpiece W, and image matching processing in steps S101, S102, and S104 according to the first embodiment.

Next, shifting of the stage 13, imaging of the workpiece W and the image matching processing in steps S101, S102 and S104 are described specifically with reference to FIG. 5. In an example shown in FIG. 5, first, an image of the image IM(1) is taken by the imaging unit 12. Next, the stage 13 is shifted in parallel in the −X axis direction by an amount of a range which is slightly smaller than a size of the one-shot imaging range of the imaging unit. 12 in the X axis direction to take images of the images IM(2) and IM(3). Next, the stage 13 is shifted in parallel in the +Y axis direction by an amount of a range which is slightly smaller than a size of the one-shot imaging range of the imaging unit 12 in the Y axis direction to take an image of the image IM(4). Then, the stage 13 is shifted in parallel in the +X axis direction by an amount of a range which is slightly smaller than a size of the one-shot imaging range of the imaging unit 12 in the X axis direction to take images of the images IM(5) and IM(6). As a result, adjacent images IM(1)-IM (6) are taken so as to include overlapping region images RIM(1)-RIM(7) that overlap one another to configure a composite portion. Subsequently, image matching is performed to match patterns inside the overlapping region images RIM(1)-RIM(7) (image matching processing). Then, the composite image IMa is generated by joining the adjacent images IM(1)-IM(6) at a position where the image matching is performed in the image matching processing. These composite image IMa, images IM(1)-IM(6), and overlapping region images RIM(1)-RIM(7) are displayed in the display unit 22.

Figure 6:
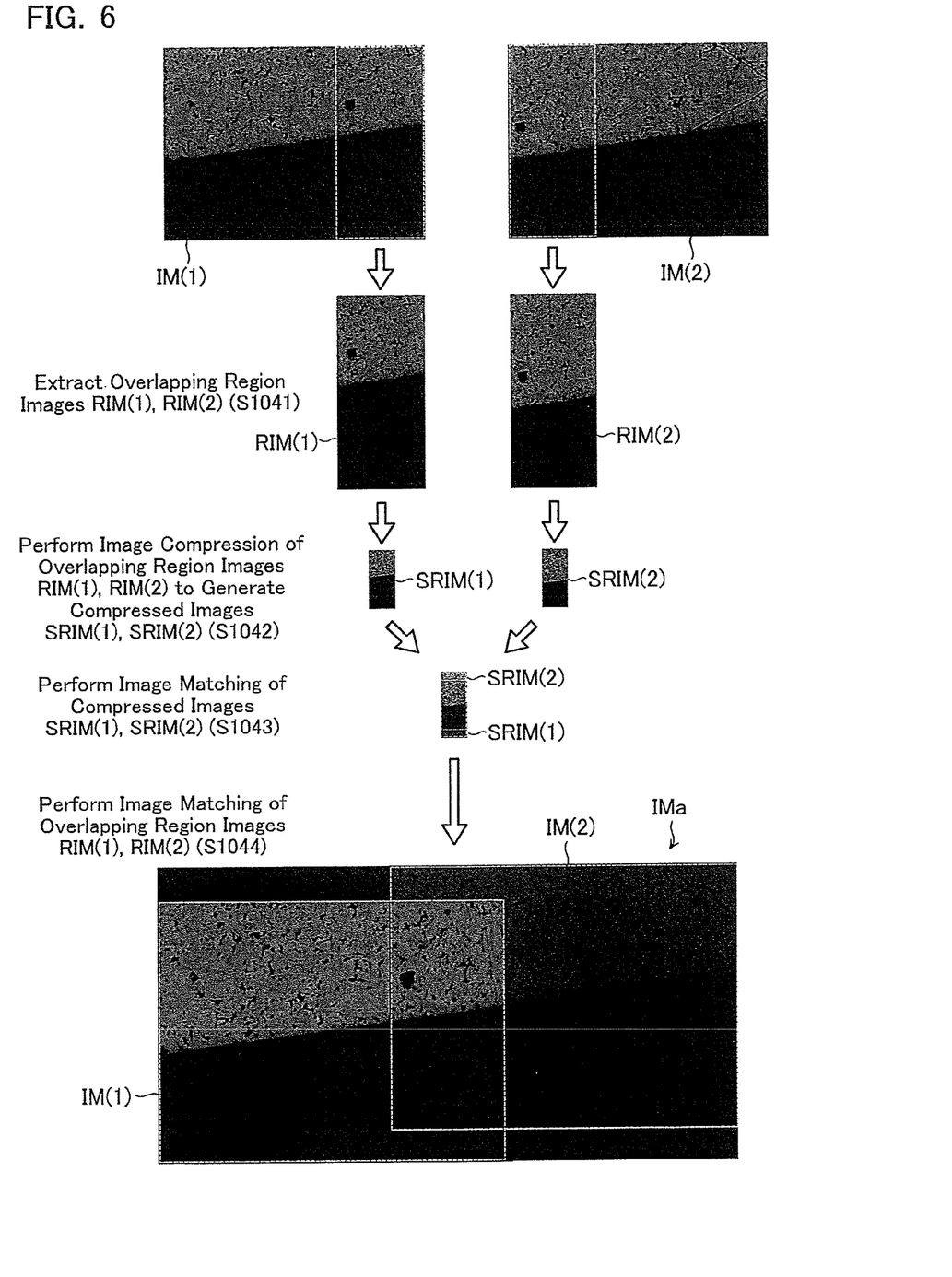
FIG. 6 is a schematic view showing the image matching processing in S104 according to the first embodiment.

Next, the image matching processing in the above-mentioned step S104 is described specifically with reference to FIG. 6. FIG. 6 shows an example where image matching is performed on the overlapping region images RIM(1) and RIM(2) of the images IM(1) and IM(2) to generate the composite image IMa. First, the overlapping region images RIM(1) and RIM(2) of the images IM(1) and IM(2) are extracted (S1041).

Then, the overlapping region images RIM(1) and RIM(2) each undergo image compression by a thinning processing or the like to generate compressed images SRIM(1) and SRIM(2) (S1042). Reducing a data amount subject to arithmetic processing in the image matching processing by this processing of step S1042 makes it possible to reduce time required in the image matching processing that follows this processing of step S1042.

Next, the fellow data-compressed compressed images SRIM(1) and SRIM(2) undergo image matching (macro-matching) to calculate a misalignment amount between the images IM(1) and IM(2) (relative position between the compressed images) (S1043). The two images IM(1) and IM(2) can be joined based on this misalignment amount to obtain the composite image IMa. When matching processing is to be performed even more accurately, it is preferable to perform image matching (micro-matching) using the pre-compression overlapping region images RIM(1) and RIM(2) in the images IM(1) and IM(2) with this misalignment amount as an initial value (S1044). This allows searching to be commenced from a vicinity of a final matching position, hence enables the misalignment amount of the two images IM(1) and IM(2) to be more accurately obtained by a small amount of processing, whereby a composite image IMa having no discontinuous portion can be generated based on this misalignment amount.

Figure 7:
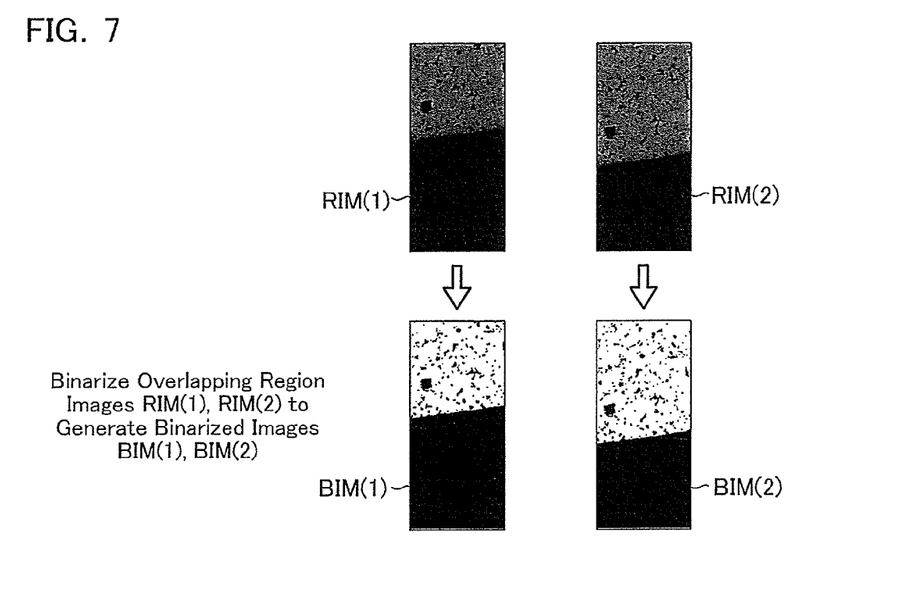
FIG. 7 is a schematic view showing the image matching processing in S104 according to the first embodiment.

Note that, in addition to the above-described processing, or in place of the image matching (S1042, S1043, S1044), a processing of the kind shown in FIG. 7, for example, may be performed. That is, the overlapping region images RIM(1) and RIM(2) are each binarized into a region of high brightness and a region of low brightness based on a certain threshold value to generate binarized images BIM(1) and BIM(2). Next, the fellow binarized images BIM(1) and BIM(2) undergo image matching (macro-matching) to calculate a misalignment amount between the images IM(1) and IM(2) (misalignment amount between the binarized images). The two images IM(1) and IM(2) can be joined based on this misalignment amount to obtain the composite image IMa. When matching processing is to be performed even more accurately, it is preferable to then perform image matching (micro-matching) of a fine pattern in the region of high brightness in the overlapping region images RIM(1) and RIM(2) with this misalignment amount as an initial value, and thereby calculate a final misalignment amount between the images IM(1) and IM(2). Then, a composite image IMa having no discontinuous portion can be generated based on this misalignment amount.

Figure 8:
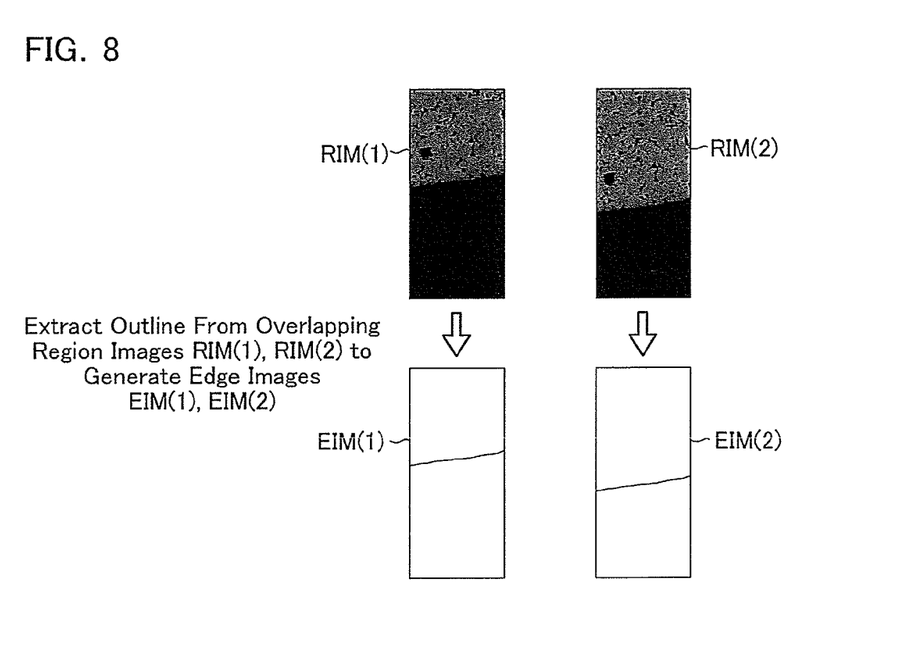
FIG. 8 is a schematic view showing the image matching processing in S104 according to the first embodiment.

Moreover, in addition to the above-described processing, or in place of the image matching (S1042, S1043, S1044), a processing of the kind shown in FIG. 8, for example, may be performed. That is, edge images EIM(1) and EIM(2) are generated, the edge images EIM(1) and EIM(2) having an outline (edge) only of an image extracted from each of the overlapping region images RIM(1) and RIM(2). Next, the fellow edge images EIM(1) and EIM(2) undergo image matching (macro-matching) to calculate a misalignment amount between the images IM(1) and IM(2) (misalignment amount between the edge images). The two images IM(1) and IM(2) can be joined based on this misalignment amount to obtain the composite image IMa. When matching processing is to be performed even more accurately, it is preferable to perform image matching (micro-matching) of the overlapping region images RIM(1) and RIM(2) in the images IM(1) and IM(2) with this misalignment amount as an initial value. Even this kind of processing allows a composite image IMa having no discontinuous portion to be generated.

Figure 9:
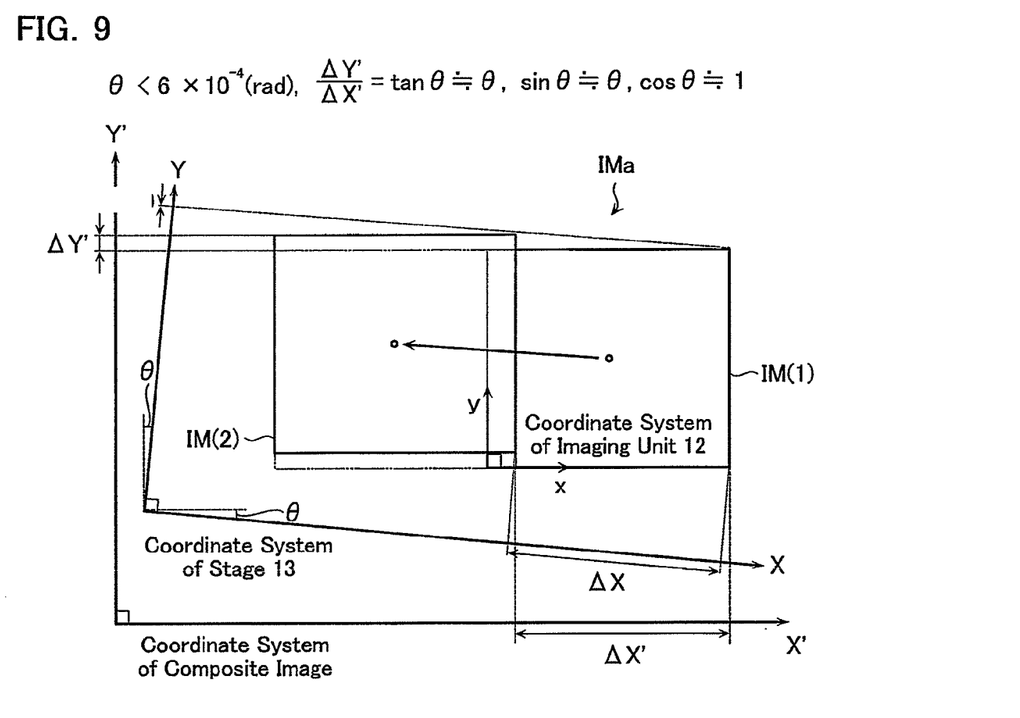
FIG. 9 is a schematic view showing calculation of a stage shifting amount in step S105 according to the first embodiment.

Next, calculation of the stage shifting amount in the above-mentioned step S105 is described specifically with reference to FIG. 9. FIG. 9 shows an example where the stage shifting amount in the X axis and Y axis directions in which the stage 13 is shiftable is calculated based on the misalignment amount between the image IM(1) and the image IM(2) in the composite image IMa. Now, a coordinate system (X', Y') is set in the composite image IMa. An axis X' and an axis Y' in the coordinate system (X', Y') of the composite image are mutually orthogonal and are set parallel to the axis x and the axis y, respectively, in the coordinate system (x, y) of the imaging unit 12. On the other hand, as mentioned above, the coordinate system (X, Y) of the stage 13 is misaligned with the coordinate system (x, y) of the imaging unit 12 by an angle $\theta$, hence the coordinate system (X', Y') of the composite image IMa is also misaligned with the coordinate system (X, Y) of the stage 13 by the angle $\theta$.

In the example shown in FIG. 9, the misalignment amount of the image IM(2) with respect to the image IM(1) in the composite image IMa when the stage 13 is shifted by an amount of LX in the X axis direction is assumed to be $\Delta X'$, and the misalignment amount in the Y axis direction is assumed to be $\Delta Y'$. The stage shifting amounts $\Delta X$ and $\Delta Y$ are obtained with respect to these $\Delta X'$ and $\Delta Y'$ in view of the angle $\theta$. In this case, since the angle $\theta$ is assumed to be an extremely small value (for example, less than $6\times10^{-4}$ rad), the angle $\theta$ may be obtained by an approximation formula "$(\Delta Y'/\Delta X')=\tan\theta\approx\theta$". Also, "$\sin\theta\approx\theta$" and "$\cos\theta\approx1$". It can be understood from these that the stage shifting amount $\Delta X$ in the X axis direction and the stage shifting amount $\Delta Y$ in the Y axis direction need only have original shifting amounts $\Delta X_0$ and $\Delta Y_0$ increased or decreased by amounts of $\Delta Y_0 \cdot \theta$ in the X axis direction and $\Delta X_0 \cdot \theta$ in the Y axis direction. These stage shifting amounts $\Delta X$ and $\Delta Y$ allow the stage 13 to be shifted along a path designated by the coordinate system (X', Y') of the composite image.

As described above, the present embodiment makes it possible to generate a composite image IMa having no discontinuity at a composite portion, easily and at low cost, without adjusting the coordinate system of the stage 13 and the coordinate system of the imaging unit 12. The present embodiment also makes it possible to shift the stage 13 accurately based on the coordinate system of the composite image by calculating the stage shifting amount.

Second Embodiment

Next, a hardness testing device according to a second embodiment is described with reference to FIG. 10. The hardness testing device according to the second embodiment includes a hardness testing machine 30 different to that in the first embodiment. The second embodiment differs from the first embodiment in this point only, and is similar to the first embodiment regarding other configurations and operation.

Figure 10:
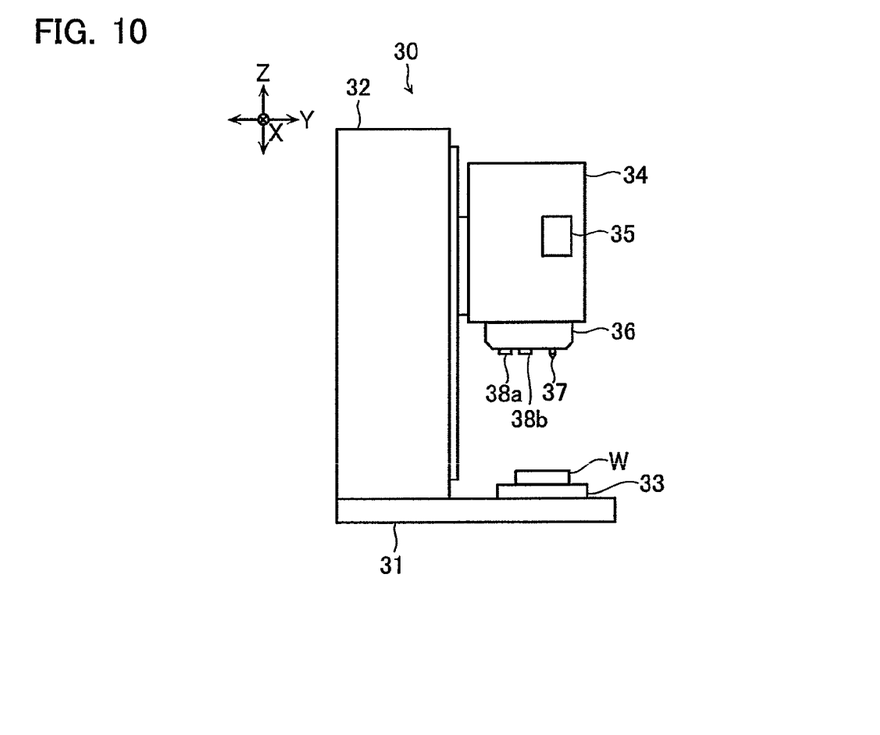
FIG. 10 is a schematic view showing a hardness testing machine 30 according to a second embodiment.

As shown in FIG. 10, the hardness testing machine 30 includes a base 31 and a support 32 extending in a Z direction from the base 31. Provided on an upper surface of the base 31 is a stage 33 shiftable in an X direction and a Y direction. The stage 33 is configured such that its upper surface is mountable with the workpiece W. Provided to a side surface of the support 32 is a unit 34 shiftable in the Z direction.

The unit 34 is provided with an imaging unit 35 and a turret 36. The imaging unit 35 takes an image of the workpiece W mounted on the stage 33. The turret 36 is provided at a lower end of the unit 34, is configured rotatable around a turret rotating shaft parallel to the Z axis, and includes on its lower side an indenter 37 and objective lenses 38a and 38b for configuring an image optical system along with the imaging unit 35. Similar advantages to those of the first embodiment are displayed, even with the above-described hardness testing machine 30 according to the second embodiment.

Third Embodiment

Figure 11:
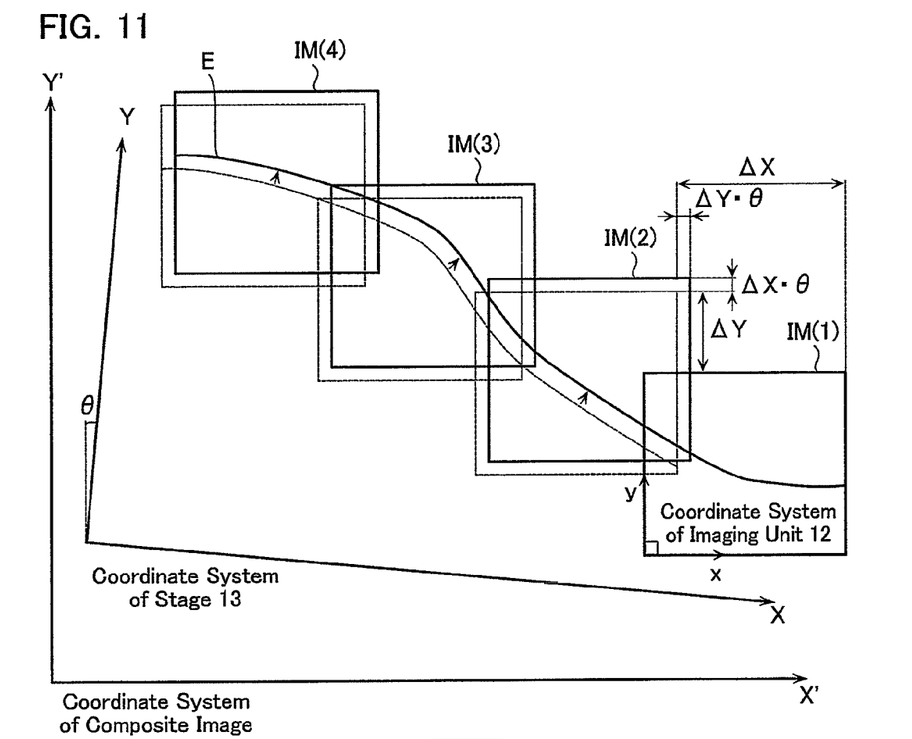
FIG. 11 is a schematic view showing shifting of the stage 13 along an edge E of the workpiece W, and imaging of the workpiece W according to a third embodiment.

Next, a hardness testing device according to a third embodiment is described. The hardness testing device according to the third embodiment differs from that of the first embodiment in a method of shifting of the stage 13 only. Now, in the above-described first embodiment, an image of a designated region of the workpiece W is taken. In contrast, in the third embodiment, as shown in FIG. 11, an edge E of the workpiece W is tracked based on an image taken beforehand (edge tracking processing), and an image is taken of images IM(1)-IM(4) along that edge E. Then, in the third embodiment, the previously mentioned image matching is executed on those images IM(1)-IM (4) to generate the composite image IMa.

Figure 12:
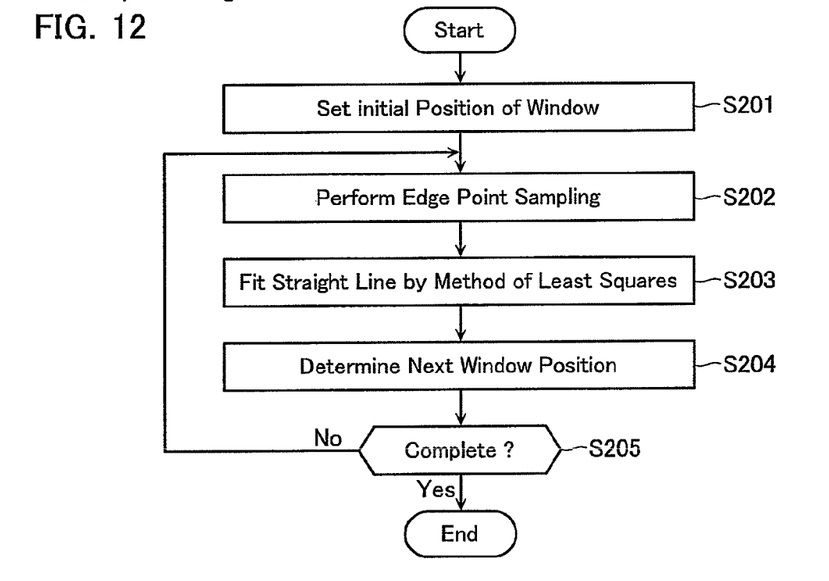
FIG. 12 is a flowchart showing an edge tracking processing according to the third embodiment.
Figure 13:
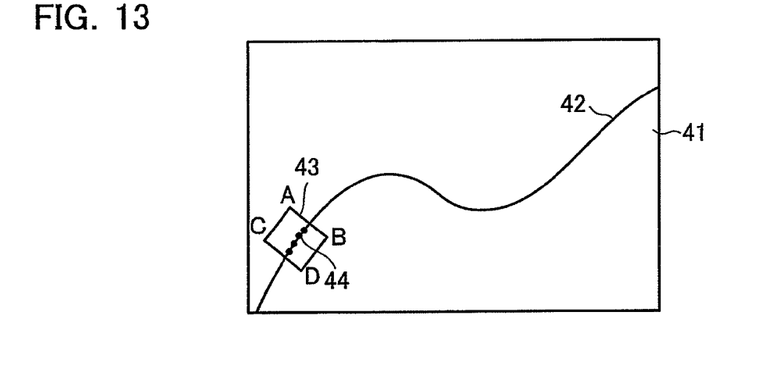
FIG. 13 is a view showing a display screen according to the third embodiment.

Next, the edge tracking processing is described with reference to FIGS. 12 and 13. FIG. 12 is a flowchart showing the edge tracking processing, and FIG. 13 is a view for explaining this processing and shows image information 41 indicating a part of the workpiece W displayed in the display unit 22. The image information 41 shown in FIG. 13 includes an edge 42 which is attempting to be tracked. Therefore, first, the mouse 24 and so on are operated to set an initial position of a rectangular window 43 indicating a measuring region so as to include a part of the edge 42 inside the window 43 (FIG. 12, S201). For example, as shown in FIG. 13, the window 43 is designated by the likes of an operation that sets four corners A, B, C, and D of the window 43 by click operation of the mouse 24, or an operation that, after designating two points at opposing corner directions of the rectangle, inclines that rectangular region at any angle to shift the rectangular region by a drag operation. Note that, at this time, a direction for tracking along the edge 42 is also designated.

Figure 14:
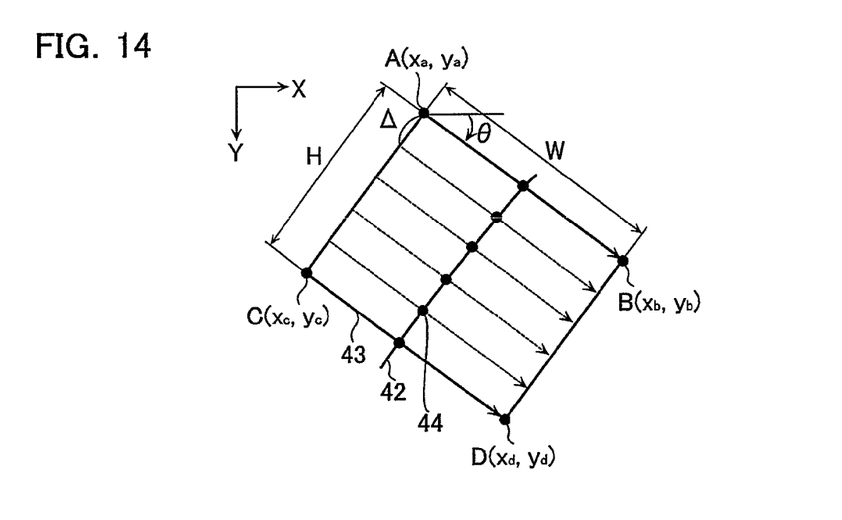
FIG. 14 is a view showing edge point detection in a window according to the third embodiment.

When the initial position of the window 43 is set, next, a plurality of edge points 44 are detected from multi-value image information in the window 43 (FIG. 12, S202). FIG. 14 shows details of this sampling. An interval $\Delta$ of sampling of the edge points shown in FIG. 14 is set previously. First, as shown in FIG. 14, multi-value image information of an address indicated by x and y coordinates is extracted, from a start point $A(x_a, y_a)$ to an end point $B(x_b, y_b)$, while changing an x coordinate $\cos \theta$ at a time [where $\theta$ is an inclination of the window 43] and a y coordinate $\sin \theta$ at a time. An appropriate threshold level is set from the obtained multi-value point sequence data, and sampling is performed, the sampling setting a point where this threshold level and the point sequence data intersect as an edge point. Next, the start point and the endpoint are shifted by amounts of $\Delta \cdot \sin \theta$ and $\Delta \cdot \cos \theta$, respectively, and similar sampling is executed. When the above processing is performed successively to a start point C $(x_c, y_c)$ and end point D $(x_x, y_d)$, sampling of the plurality of edge points 44 at the previously set interval $\Delta$ is completed.

Figure 15:
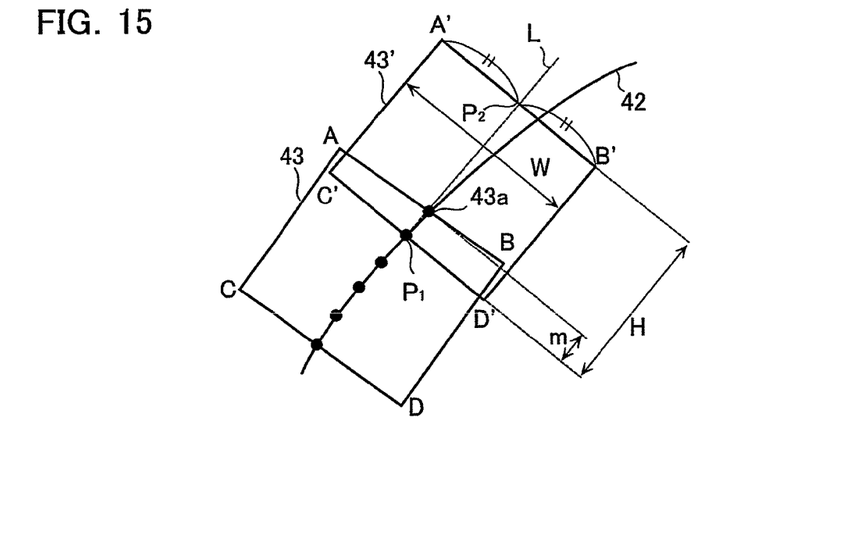
FIG. 15 is a view showing a determining sequence of window positions according to the third embodiment.

Next, an approximate line is fitted to sampling values of the obtained plurality of edge points 44 by, for example, a method of least squares (FIG. 12, S203). Now, as shown in FIG. 15, if an approximate line L is assumed to be obtained from the sampling values of the edge points 44 obtained by the window 43, then a next window 43' is determined so as to conform with this approximate line L (FIG. 12, S204). Therefore, first, a perpendicular line is dropped to the approximate line L from an edge point 43a nearest to an edge in the shifting direction of the window 43 obtained by the present window 43, then a point $P_1$ and a point $P_2$ are obtained, the point $P_1$ being separated from a crossing point of the perpendicular line and the approximate line L by an amount of $H \cdot m/100$ (where H is a height of the window and m is a previously set duplication rate (%)) along the approximate line L in an opposite direction to the shifting direction of the window 43, and the point $P_2$ being separated from the point $P_1$ by an amount of H in the shifting direction of the window 43. Next, points that are on lines orthogonal to the approximate line L at each of points $P_1$ and $P_2$ and that are each separated from the approximate line L by an amount of W/2 (where W is a width of the window) are set as points A', B', C', D' and at four corners of a new window 43'. As a result, the next window 43' is determined.

When the next window 43' is determined, the window 43 is shifted sequentially while performing sampling of edge points and fitting of an approximate line in the window 43' similarly to as previously mentioned. Then, when the edge to be tracked is all tracked, the processing is completed (FIG. 12, S205).

This concludes description of embodiments of the present invention, but it should be noted that the present invention is not limited to the above-described embodiments, and that various alterations, additions, and so on, are possible within a range not departing from the scope and spirit of the invention. For example, disposition of the indentation position may also be based on the likes of CAD data or shape data of a workpiece of a profile measuring instrument.

In addition, shifting of the stages 13 and 33, and the unit 34 may also be performed manually. Moreover, when any position on the composite image IMa displayed in the display unit 22 is designated by an operator by the keyboard 23 and the mouse 24, an image of that designated position may also be taken by the imaging unit 12.

What is claimed is:

1. An image processing device, comprising:
   an imaging unit for taking an image of a measuring object;
   a stage configured to be mountable with the measuring object and to be shiftable relatively with respect to the imaging unit; and
   a control unit for shifting the imaging unit relatively with respect to the stage to take the image of the measuring object at a plurality of places by the imaging unit and thereby obtain a plurality of images, and for generating a composite image of the measuring object having a range which is wider than an imaging range of the imaging unit by combining the obtained plurality of images or images obtained by a certain processing from the obtained plurality of images,
   the control unit shifting the imaging unit relatively with respect to the stage such that parts of images adjacent to one another obtained by the imaging unit overlap,
   the control unit performing an image matching processing that performs image matching of an overlapping portion of the adjacent images,
   the control unit generating the composite image of the measuring object by joining the adjacent images at a position where the image matching is performed in the image matching processing, and
   the control unit calculating an angular misalignment amount of coordinates in the composite image and the stage by the image matching processing, and controlling angular shifting of the imaging unit with respect to the stage based on the misalignment amount.

2. The image processing device according to claim 1, wherein the control unit performs image compression of the overlapping portion to generate a compressed image, and performs the image matching processing to the compressed image.

3. The image processing device according to claim 1, wherein the control unit binarizes the overlapping portion to generate a binarized image, and performs the image matching progressing to the binarized image.

4. The image processing device according to claim 1, wherein the control unit extracts an outline of the overlapping portion to generate an edge image, and performs the image matching processing to the edge image.

5. The image processing device according to claim 1, wherein the control unit performs image compression of the overlapping portion to generate a compressed image, performs image matching of fellow compressed images to obtain a relative position between the compressed images, and executes the image matching processing with the relative position between the compressed images as an initial value.

6. The image processing device according to claim 1, wherein the control unit binarizes the overlapping portion to generate a binarized image, performs image matching of fellow binarized images to obtain a relative position between the binarized images, and executes the image matching processing with the relative position between the binarized images as an initial value.

7. The image processing device according to claim 1, wherein the control unit extracts an outline of the overlapping portion to generate an edge image, performs image matching of fellow edge images to obtain a relative position between the edge images, and executes the image matching processing with the relative position between the edge images as an initial value.

8. The image processing device according to claim 1, wherein
the control unit sets a window in an image that includes an edge such that a part of the edge is included in the window, detects a plurality of edge points in the set window from image information in the set window, fits an approximate line to the detected plurality of edge points, and sets a next new window such that a partial region of the new window overlaps a current window along the fitted approximate line, and
the control unit, by repeating sequentially detection of the edge points, fitting of the approximate line, and generation of the new window based on the image information in the new window, extracts required measurement points in the window while shifting the window along the edge of the image.

9. The image processing device according to claim 1, further comprising:
an indenter for making an indentation in the measuring object,
wherein the control unit receives designation of a position for making the indentation based on the composite image.

10. The image processing device according to claim 9, further comprising:
a plurality of objective lenses for the imaging unit; and
a turret for disposing the indenter and the plurality of objective lenses at a certain position.

11. An image processing device, comprising:
an imaging unit for taking an image of a measuring object;
a stage configured to be mountable with the measuring object and to be shiftable relatively with respect to the imaging unit; and
a control unit for shifting the imaging unit relatively with respect to the stage to take the image of the measuring object at a plurality of places by the imaging unit and thereby obtain a plurality of images,
the control unit shifting the imaging unit relatively with respect to the stage such that parts of images adjacent to one another obtained by the imaging unit overlap,
the control unit performing an image matching processing that performs image matching of an overlapping portion of the adjacent images, and
the control unit calculating an angular misalignment amount of coordinates in the composite image and the stage by the image matching processing, and controlling angular shifting of the imaging unit with respect to the stage based on the misalignment amount.

12. The image processing device according to claim 11, wherein the control unit performs image compression of the overlapping portion to generate a compressed image, and performs the image matching processing to the compressed image.

13. The image processing device according to claim 11, wherein the control unit binarizes the overlapping portion to generate a binarized image, and performs the image matching processing to the binarized image.

14. The image processing device according to claim 11, wherein the control unit extracts an outline of the overlapping portion to generate an edge image, and performs the image matching processing to the edge image.

15. A method of image processing, in which an imaging unit for taking an image of a measuring object and a stage configured to be mountable with the measuring object and to be shiftable relatively with respect to the imaging unit are employed to shift the imaging unit relatively with respect to the stage to take the image of the measuring object at a plurality of places by the imaging unit and thereby obtain a plurality of images, and to generate a composite image of the measuring object having a range which is wider than an imaging range of the imaging unit by combining the obtained plurality of images or images obtained by a certain processing from the obtained plurality of images, the method comprising:
shifting the imaging unit relatively with respect to the stage such that parts of images adjacent to one another obtained by the imaging unit overlap;
performing an image matching processing that performs image matching of an overlapping portion of the adjacent images;
generating the composite image of the measuring object by joining the adjacent images at a position where the image matching is performed in the image matching processing;
calculating an angular misalignment amount of coordinates in the composite image and the stage by the image matching processing; and
controlling angular shifting of the imaging unit with respect to the stage based on the misalignment amount.

16. The method of image processing according to claim 15, further comprising:
performing image compression of the overlapping portion to generate a compressed image, and performing the image matching processing to the compressed image.

17. The method of image processing according to claim 15, further comprising:
binarizing the overlapping portion to generate a binarized image, and performing the image matching processing to the binarized image.

18. The method of image processing according to claim 16, further comprising:
extracting an outline of the overlapping portion to generate an edge image, and performing the image matching processing to the edge image.

* * * * *